United States Patent [19]

Genese

[11] 4,078,565
[45] Mar. 14, 1978

[54] READILY ACTIVATED HYPODERMIC SYRINGE

[75] Inventor: Joseph Nicholas Genese, Waukegan, Ill.

[73] Assignee: Abbott Laboratories, North Chicago, Ill.

[21] Appl. No.: 729,320

[22] Filed: Oct. 4, 1976

[51] Int. Cl.² ............................................. A61M 5/00
[52] U.S. Cl. ................................ 128/220; 128/218 N
[58] Field of Search .................... 128/220, 221, 218 R, 128/218 N, 218 D, 215

[56] References Cited

U.S. PATENT DOCUMENTS

| 2,834,346 | 5/1958 | Adams | 128/218 N |
| 2,880,725 | 4/1959 | Kendall | 128/218 N |
| 2,902,995 | 9/1959 | Loper | 128/215 |
| 3,043,304 | 7/1962 | Higgins | 128/218 N |

FOREIGN PATENT DOCUMENTS

| 1,286,690 | 8/1972 | United Kingdom | 128/218 N |

*Primary Examiner*—John D. Yasko

*Attorney, Agent, or Firm*—Robert L. Niblack; Neil E. Hamilton

[57] ABSTRACT

A prefilled, readily activated syringe of the disposable type which can be activated in a fast and efficient manner. A vial containing the medicament to be administered is positioned in a syringe barrel and spaced from one point of a double piercing cannula member which is slidably received in the opposing end of the syringe barrel. Resilient finger gripping members engage a groove in the hub of the piercing cannula in one position with the piercing point spaced from the vial stopper. To activate the syringe one merely moves the slidable cannula member in a direction toward the vial wherein the finger gripping members are released from the first annular groove and engage a second annular groove spaced from the first. To provide needle point alignment and to prevent rotation during movement of the piercing cannula one of the finger gripping members rides in a groove which intersects the two annular grooves and also engages an open portion in a stop member which is positioned adjacent the end of the second groove.

21 Claims, 6 Drawing Figures

READILY ACTIVATED HYPODERMIC SYRINGE

BACKGROUND OF THE INVENTION

This invention relates to prefilled, readily activated syringes. More particularly, this invention relates to a means for activating a prefilled, readily activated syringe which requires a minimum amount of effort and provides positive activation.

The type of syringe concerned with this invention is described in U.S. Pat. Nos. 3,378,008 and 3,376,866. In these patents, a threaded engagement is effected between the stopper in a vial and the syringe body which activates the syringe by means of a central cannula member which will pierce through the stopper vial as the vial is threadably moved over the piercing cannula. This type of threaded activation poses problems in that time must be spent turning the vial prior to activation. Further, if the vial is carried on the syringe by partially engaging the threads, premature activation could occur as it is difficult to determine how far to thread the vial onto the syringe without piercing the vial stopper. Consequently this syringe unit is marketed with the vial separated from the syringe body. This means that additional time must be utilized to activate the syringe because the two components must be threaded together prior to activation. Automatic type activated syringes are disclosed in U.S. Pat. Nos. 3,320,955; 3,330,279 and 3,825,003. All of these particular units utilize spring tensioning means in order to activate the cannula and drive it through a piercing stopper. These particular mechanisms are costly to manufacture as are the screw-type means for accomplishing the same purpose as described in U.S. Pat. No. 3,115,135 for the purpose of engaging a cartridge as well as a piston member to form a disposable syringe. However, nowhere in the prior art is there indicated the utilization of expandable finger members which can engage in a positive manner a groove or resistance means in one position on the hub of a piercing cannula member to prevent accidental puncture yet also afford positive puncture when the cannula is moved to another position to engage additional resistance means or a groove.

It is an advantage of the present invention to provide a prefilled, readily activated syringe which affords quick and positive activation; a readily activated syringe which can be fabricated from a minimum number of parts; a prefilled, readily activated syringe which provides cannula alignment and prevents nonrotation and positive movement of the piercing cannula with a minimum amount of effort; a prefilled, disposable readily activated syringe which is easily molded and at a minimum amount of cost.

SUMMARY OF THE INVENTION

The foregoing objects are accomplished and the shortcomings of the prior art are overcome by the present prefilled, readily activated syringe which comprises a holder or barrel member defining a tubular chamber and having an open end and a closed end defining a nozzle with a passage therein. A small volume container or vial is constructed and arranged to fit within the tubular chamber in a sliding relationship and has a pierceable stopper in sealing engagement with the vial. A double pointed piercing cannula member has a hub portion which is disposed in sliding engagement in the nozzle portion. Resilient finger gripping members extend from either the nozzle or the hub portion and are biased toward each other having flange portions extending from the ends of the finger gripping members. First and second resistance means, preferably in the form in indentations or annular grooves are carried by either the hub or the nozzle so that the flange portions of the finger gripping members engage the first resistance means in one instance and then can be moved into contact with the second resistance means in another. The cannula member extends from the nozzle portion with one of the piercing points spaced from the stopper vial when the fingers engage the first resistance member and then move through and pierce the stopper when the finger gripping members engage the second resistance means. In a preferred embodiment, the resilient finger members extend from the hub portion of the syringe and annular groove members are spaced on the hub of the piercing cannula with an additional slot intersecting the two grooves for engagement by flange portion of one of the finger members so as to provide alignment of and to prevent rotation of the piercing cannula as it slides in the nozzle portion of the syringe. Also preferably formed at the end of the second resistance means is a stop member to positively engage the ends of some of the resilient finger members and prevent further movement as well as having an opening to receive the flange of a longer extending finger to prevent rotation of the cannula at the end of its travel.

BRIEF DESCRIPTION OF THE DRAWINGS

A better understanding of the present prefilled, readily activated syringe will be accomplished by reference to the drawing wherein.

DESCRIPTION OF THE PREFERRED EMBODIMENT

Figure 2:
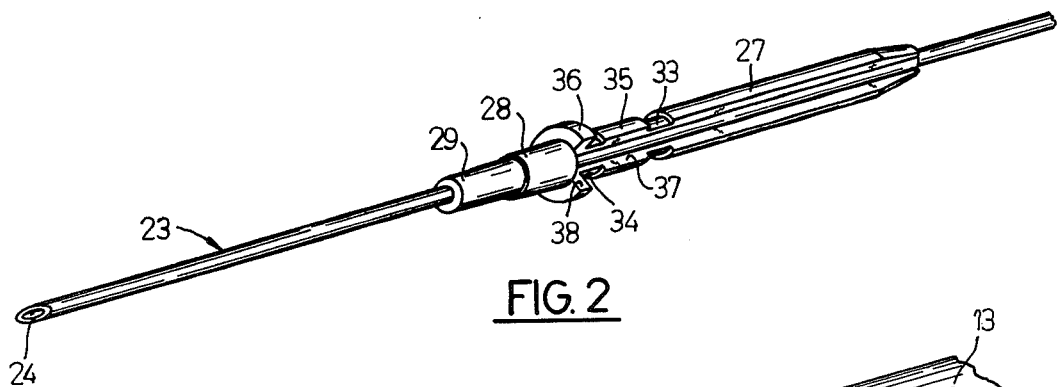
FIG. 2 is a perspective view of the double-pointed cannula member removed from the syringe barrel in FIG. 1.

Proceeding to a detailed description of a preferred embodiment of the present invention, the prefilled, readily activated syringe 10 has a barrel member 12 formed from a tubular chamber 13 terminating in a closed end 15 and defining a nozzle portion 16. Extending from the nozzle portion, are a plurality of resilient finger members 30 for engaging a double-pointed cannula member generally 23 having a hypodermic piercing point 24 and a cannula hub 27 formed with two reduced diameter sections 28 and 29. A first resistance means in the form of an indentation or annular groove 33 is provided in cannula hub 27 as well as a second resistance means in the form of a second and spaced annular groove 34. Intersecting the two annular grooves is a longitudinally positioned slot 37. It will be noted that slot 37 extends from a circumferentially extending stop member 36 and longitudinally along the remaining portion of cannula hub 27 opposite the stop. As best seen in FIG. 2, stop member 36 is formed with a generally V-shaped open section 38 which is longitudinally aligned and coextensive with slot 37 which also has a substantially V-shaped configuration. Open section 38 is aligned with the bevel of piercing point 24 and with slot 37 for purposes as will be explained later in the Operation.

Figure 1:
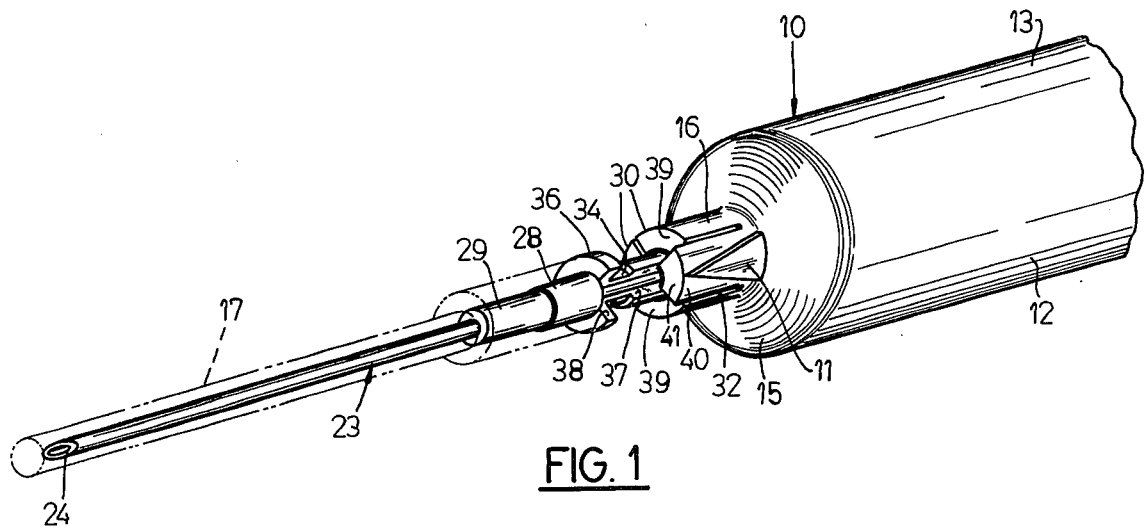
FIG. 1 is a partial perspective view of the prefilled, readily activated syringe illustrating the resilient finger members at the end of the syringe barrel and engaging the movable cannula member in a first position.
Figure 3:
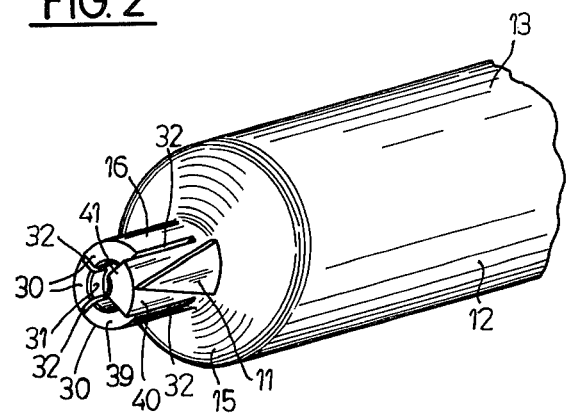
FIG. 3 is a partial perspective view of the syringe barrel illustrating the resilient finger members and with the piercing cannula removed therefrom.

In FIGS. 1 and 3, it will be noted that the resilient fingers 30 substantially surround hub 16 and are separated by slots 32. All of the fingers have flange portions 31 and it will be noted that one of the fingers 40 is longer than the others and also has a flange portion 41 to result in a generally V-shaped or arcuate configuration. Finger 40 has a raised portion 11 in the form of an arrow to indicate alignment with open section 38 and consequently cannula point 24.

Figure 4:
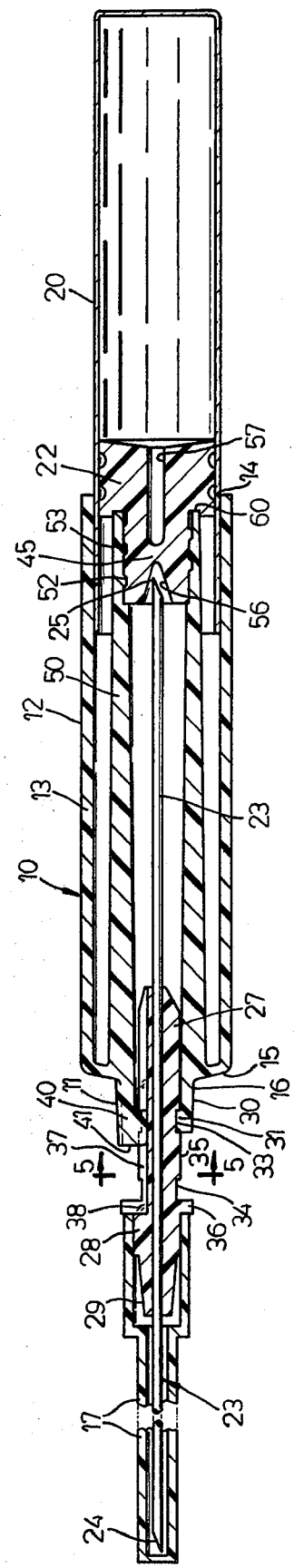
FIG. 4 is a view in vertical section of the prefilled, readily activated syringe shown in FIG. 1 as it would appear prior to activation.
Figure 5:
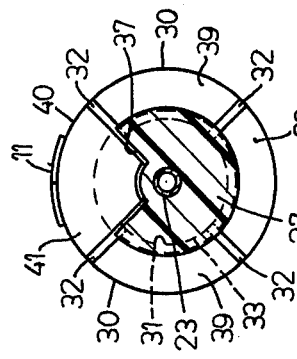
FIG. 5 is a view in vertical section taken along line 5—5 of FIG. 4.
Figure 6:
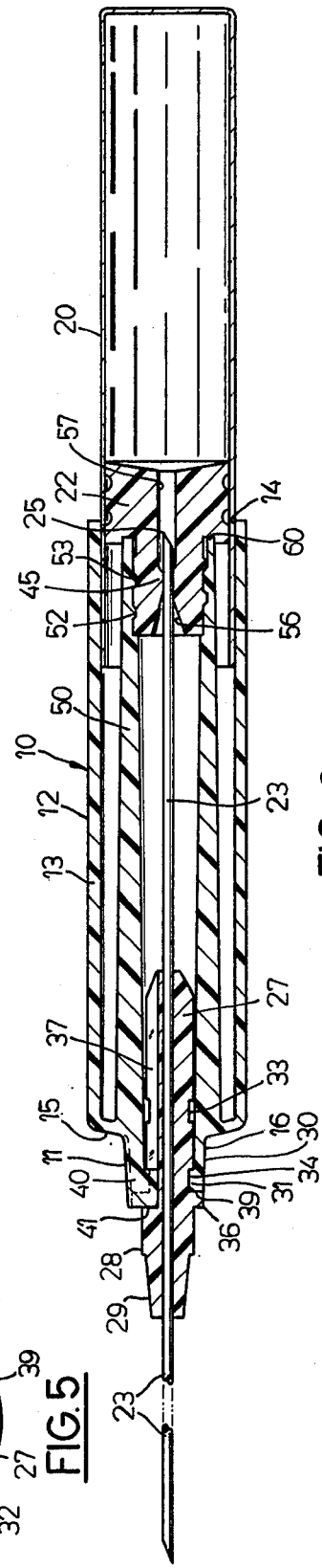
FIG. 6 is a view similar to FIG. 4 except showing the readily activated syringe after it is activated.

Referring to FIGS. 4 and 6, it will be seen that a small volume container in the form of a vial 20 is secured to barrel 12 by external threads 53 formed on pierceable stopper 22 which is sealed in vial 20. Barrel 12 has a central chamber 50 with internal complementary threads 52 formed near the open end of the chamber and the open end 14 of the syringe barrel 12 to engage threads 53. This threaded arrangement and interlocking means for the vial and barrel are as described in U.S. Pat. No. 3,376,866. It will be seen that stopper 22 has a conical passage 56 and an opposing longitudinal passage 57 with a barrier 45 formed in between as part of stopper 22. It will be further noted that central chamber 50 has a shoulder portion 60 for abutment against an end portion of stopper 22 when it is fully threaded onto chamber 50. It will be seen that when stopper 22 is fully threaded onto chamber 50, the stopper piercing point 25 of cannula member 23 will be disposed in conical passage 56 and out of contact with the barrier section 45.

FIG. 6 illustrates the prefilled, readily activated syringe 10 after it is activated. It will be noted that the piercing point 25 is now positioned in the longitudinal passage 57. This is effected by movement of cannula member 23 in the direction of vial 20 and further into the barrel member 12 by means of cannula hub 27 sliding inside central chamber 50 in a manner which will now be described.

OPERATION

A better understanding of the advantage of the prefilled, readily activated syringe 10 will be had by a description of its operation. The unit will be assembled as described in FIG. 4 with barrel 12 serving as a holding means for vial 20. In this position, vial 20 will be positioned on barrel 12 with the stopper threads 53 engaging the internal threads 52 of inner chamber 50. As thus positioned, stopper 22 will abut against the shoulder 60 in the chamber. At the opposing end, the double-pointed cannula member 23 will be positioned such that the flange portions 31 of the resilient fingers 30 will engage groove 33 and flange portion 41 of the longer finger member 40 will be disposed in slot 37. This will automatically align arrow 11 with the needle point 24 and be an immediate indication of the point while enclosing in cover 17. In this position (as shown in FIG. 4), the piercing point 25 will be positioned in the conical passage 56 of stopper 22 and the cannula member 23 will be held in a relatively stationary position.

When it is desired to activate the prefilled syringe 10, all that is required is that the needle cover 17 be grasped and moved in the direction of barrel member 12. Cover 17 will effect contact with stop 36 and move cannula hub 27 of cannula member 23 inwardly in the syringe barrel. This movement of the cannula hub 27 will cause the flanges 31 of the finger members 30 to ride up and out of annular groove 33, over the section 35 between grooves 33 and 34 of hub 37 and into groove 34. The movement will continue until the ends 39 of the finger members 30 will abut against stop member 36 and the flange 41 on the longer extending finger 40 will come to rest in open section 38 of stop 36. The unit will then appear as in FIG. 6 with the needle cover 17 removed.

It will be noted that with the foregoing movement, the piercing end 25 of cannula member 23 will have moved through the barrier portion 45 of stopper 22 and into the longitudinal passage 57. Communication will now be made between the inside of vial 20 and the end point 24 of the cannula which serves as a hypodermic needle. The needle cover 17 will then be removed and the syringe utilized in the usual manner with the contents of vial 20 being expelled from end 24 by moving vial 20 slidably over inner chamber 50 as afforded by the spacing of inner chamber 50 and tubular chamber 13. This movement is facilitated by placement of the operator's fingers on the usual finger grips (not shown, which will be oppositely disposed to arrow 11) and the thumb on the end of vial 20 opposite the syringe barrel 12. During the preceding piercing of the stopper vial 22 and movement of the vial, it should be noted that stopper 22 will be held in a stationary manner in barrel 12 by means of the interlocking means formed in part by threads 52 and 53 and stopper 22 will slide in a sealing manner inside vial 20.

Most importantly, it will be noted that nonrotation of cannula member 23 with respect to syringe barrel 12 and fingers 30 is afforded by flange 41 of finger 40 riding in V-shaped slot 37 and ultimately being positioned in V-shaped opening in stop 38. This provides positive puncture of stopper 22 and stop 38 prevents excessive movement of cannula member 23 after puncture by contact with the ends 39 of fingers 31. Further, the nonrotation feature of cannula member 23 also assures that cannula point 24 will at all times be aligned with arrow 11 so that the operator will know the position of the point during activation of the syringe and can make the injection immediately without further manipulation.

While a multiplicity of resilient fingers 30 are indicated as extending from barrel member 12, the unit could be utilized with only one finger although the same positive action of cannula member 23 would not be accomplished. Stop member 36 prevents further movement of the cannula member 23 and its piercing point 25 inside stopper 22, it also could be eliminated if sufficient engagement is provided by the finger members in the groove 34. While the longer finger member 40 and its engagement with slot 37 and the open notch 38 in the stop afford a nonrotation mechanism for the double-pointed cannula, this also could be eliminated. Further, grooves 33 and 34 provide the preferred resistance means for the double positioning of the slidable cannula in conjunction with the resilient fingers 30, annular ridges could be substituted although these are not as desirable because ridges would not prevent reverse movement. Threads 52 and 53 provide an interlocking means for vial 20 in barrel 20. However any suitable frictional engagement could be substituted such as a snap-fit arrangement.

The preferred materials for fabricating the syringe barrel 12 and the resilient fingers 30 and 40 are polypropylene, polyethylene, polyesters and nylon. Cannula hub 27 can be fabricated from polyvinylchloride, acrylonitrile styrene and polycarbonate. Other resinous materials could be substituted provided they afford the required rigidity and flexibility for operation.

It will thus be seen that through the present invention there is now provided a prefilled, readily activated syringe wherein activation is afforded in a fast and positive manner. The activation means is easily molded and is accomplished by utilizing a minimum number of parts. Previous assembly of the vial on the syringe body is eliminated yet accidental preactivation is avoided. Immediate positioning of the cannula point is indicated and maintained throughout activation of the syringe. Assembly of the activation means is easily accomplished without the requirement of precise positioning of parts such as spring members.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

What is claimed is:

1. A prefilled, readily activated syringe comprising:
holding means for a small volume container defining a nozzle portion with a passage therein;
a small volume container constructed and arranged to be engaged by said holding means in a sliding relationship;
a pierceable stopper in sealing engagement with said container;
a double-pointed piercing cannula member having a hub portion disposed in sliding engagement in the said nozzle portion;
at least one resilient finger gripping member having a contacting portion extending therefrom;
first and second resistance means spaced from each other, said finger gripping member and said first and second resistance means operatively associated with said hub portion and said nozzle portion, said contacting portion of said finger gripping member biased toward and engaging said first resistance means in one instance and the second resistance means in another, said cannula member extending from said nozzle portion with one of said piercing points spaced from said container stopper when said finger member engages said first resistance member and said piercing point piercing through said stopper when said finger gripping member engages said second resistance means.

2. A prefilled, readily activated syringe comprising:
a barrel member defining a tubular chamber having an open end and a closed end defining a nozzle portion with a passage therein;
a vial constructed and arranged to fit within said tubular chamber in a sliding relationship;
a pierceable stopper in sealing engagement with said vial;
a double-pointed piercing cannula member having a hub portion disposed in sliding engagement in said nozzle portion;
at least one resilient finger gripping member having a flange portion extending therefrom;
a first and second indentation spaced from each other, said finger gripping member and said first and second indentation operatively associated with said hub portion and said nozzle portion, said flange portion of said finger gripping member biased toward and engaging said first indentation in one instance and the second indentation in another, said cannula member extending from said nozzle portion with one of said piercing points spaced from said stopper vial when said finger member engages said first indentation and said piercing point piercing through said stopper when said finger gripping member engages the second indentation.

3. The prefilled, readily activated syringe as defined in claim 2 wherein said first and second indentations comprise annular groove members.

4. The prefilled, readily activated syringe as defined in claim 3 wherein a multiplicity of finger gripping members define said nozzle portion and said first and second grooves are defined by said hub portion of said cannula member.

5. The prefilled, readily activated syringe as defined in claim 4 further including a stop member disposed adjacent said second annular grooves remote from said vial stopper piercing point for engagement by the end surfaces of said finger gripping members.

6. The prefilled, readily activated syringe as defined in claim 5 wherein said hub portion includes a slot intersecting said grooves and one of said finger members has an extending section for sliding engagement in said slot.

7. The prefilled, readily activated syringe as defined in claim 6 wherein said stop member includes an open section and one of said finger members extends from said hub a greater distance than the others to be accommodated in said open section.

8. The prefilled, readily activated syringe as defined in claim 7 wherein said open section in said stop member and said slot extending between said grooves are coextensive.

9. The prefilled, readily activated syringe as defined in claim 8 wherein said open section in said stop member, said slot extending between said grooves and said extending portion for said one finger member which is slidably engaged by said slot are all substantially V-shaped in configuration.

10. The prefilled, readily activated syringe as defined in claim 2 further including means disposed substantially adjacent the open end of said tubular chamber to engage said pierceable stopper and retain said pierceable stopper in a stationary manner with respect to vial, said engagement means disposed to permit said vial to pass thereover.

11. The prefilled, readily activated syringe as defined in claim 10 wherein said engagement means for said stopper includes a centrally disposed chamber and said hub portion on said cannula is constructed and arranged to slide therein.

12. The prefilled, readily activated syringe as defined in claim 11 wherein said engagement means comprising complementary screw threads carried by said chamber and said vial stopper and said chamber has a shoulder for engagement with said stopper to position said stopper apart from one of said piercing points when said finger member engages said first indentation.

13. The prefilled, readily activated syringe as defined in claim 4 wherein said finger gripping members are composed of a rigid plastic composition and substantially surround said hub on said nozzle portion.

14. A syringe device adapted to receive a slidable cannula through its nozzle portion comprising:
- a holder having means at one end adapted to receive a vial and a closed end defining said nozzle portion with a passage therein;
- a plurality of outwardly positioned resilient gripping members defined from said nozzle portion and biased toward each other, said gripping members surrounding said passage having flange portions extending therefrom.

15. The syringe device as defined in claim 14 wherein one of said gripping members with said flange portion extends from said nozzle portion a greater distance than the other gripping members.

16. The syringe device as defined in claim 15 wherein said gripping members are in the form of finger members and are composed of a rigid plastic composition and substantially surround said nozzle portion.

17. The syringe device as defined in claim 16 wherein said holder comprises a tubular chamber.

18. The syringe device as defined in claim 15 further including alignment indicating means carried by the outer surface of said gripping member extending a greater distance than the other gripping members.

19. A syringe device adapted to receive a slidable cannula through its nozzle portion comprising:
- a syringe barrel defining a nozzle portion with a passage therein;
- a pierceable stopper positioned in said syringe barrel;
- a double-pointed piercing cannula member having a hub portion disposed in sliding engagement in said nozzle portion;
- at least one resilient finger gripping member having a contacting portion;
- first and second resistance means spaced from each other, said finger gripping member and said first and second resistance means operatively associated with said hub portion and said nozzle portion, said contacting portion of said finger gripping member biased toward and engaging said first resistance in one instance and the second resistance means in another, said cannula member extending from said nozzle portion with one of said piercing points spaced from said pierceable member when said finger member engages said first resistance member and said piercing point piercing through said stopper when said finger gripping member engages said second resistance means;
- an additional finger gripping member having an extending section; and
- a slot intersecting said first and second resistance means and said extending section of said additional finger gripping member constructed and arranged for sliding engagement in said slot.

20. The syringe device as defined in claim 19 further including a stop member disposed adjacent said second resistance means for engagement by the end surface of said finger gripping member.

21. The syringe device as defined in claim 20 wherein said stop member includes an open section and said additional finger gripping member can be accommodated in said open section.

* * * * *